(12) United States Patent
Biggs et al.

(10) Patent No.: US 7,069,081 B2
(45) Date of Patent: Jun. 27, 2006

(54) ONE PIECE HEADER ASSEMBLY FOR AN IMPLANTABLE MEDICAL DEVICE

(75) Inventors: James C. Biggs, East Aurora, NY (US); Norbert W. Frenz, Jr., Clarence, NY (US); David A. Faltisco, Blasdell, NY (US)

(73) Assignee: Wilson Greatbatch Ltd., Clarence, NY (US)

( * ) Notice: Subject to any disclaimer, the term of this patent is extended or adjusted under 35 U.S.C. 154(b) by 448 days.

(21) Appl. No.: 10/068,030

(22) Filed: Feb. 6, 2002

(65) Prior Publication Data
US 2002/0107554 A1 Aug. 8, 2002

Related U.S. Application Data

(60) Provisional application No. 60/267,764, filed on Feb. 8, 2001, provisional application No. 60/309,411, filed on Aug. 1, 2001.

(51) Int. Cl.
*A61N 1/18* (2006.01)
(52) U.S. Cl. ..................................................... 607/37
(58) Field of Classification Search .................. 607/36, 607/5–12, 37
See application file for complete search history.

(56) References Cited

U.S. PATENT DOCUMENTS

| | | | |
|---|---|---|---|
| 4,010,759 A | 3/1977 | Boer | |
| 4,010,760 A | 3/1977 | Kraska et al. | |
| 4,041,956 A | 8/1977 | Purdy et al. | |
| 4,057,068 A | 11/1977 | Comben | |
| 4,254,775 A | 3/1981 | Langer | |
| 4,262,673 A | 4/1981 | Kinney et al. | |
| 4,445,511 A * | 5/1984 | Cowdery et al. | 607/37 |
| 4,471,783 A | 9/1984 | Buffet | |
| 4,764,132 A | 8/1988 | Stutz, Jr. | |
| 5,086,773 A * | 2/1992 | Ware | 607/2 |
| 5,103,818 A | 4/1992 | Maston et al. | |
| 5,282,841 A | 2/1994 | Szyszkowski | |
| 5,336,246 A | 8/1994 | Dantanarayana | |
| 5,549,653 A | 8/1996 | Stotts et al. | |
| 5,643,328 A | 7/1997 | Cooke et al. | |
| 5,741,313 A | 4/1998 | Davis et al. | |
| 5,755,743 A * | 5/1998 | Volz et al. | 607/37 |
| 5,919,215 A * | 7/1999 | Wiklund et al. | 607/36 |
| 5,980,973 A | 11/1999 | Onyekaba et al. | |
| 6,026,325 A | 2/2000 | Weinberg et al. | |
| 6,052,623 A | 4/2000 | Fenner et al. | |

FOREIGN PATENT DOCUMENTS

EP 0 006 281 1/1980

* cited by examiner

*Primary Examiner*—Mark Bockelman
(74) *Attorney, Agent, or Firm*—Michael F. Scalise (57) ABSTRACT

The present invention is directed to a header assembly attachable to a medical device for the purpose of connecting its output terminals to at least one lead, the lead terminating at a target organ or portion of the body intending to be assisted. A number of leads are connectable to the header, including single and coaxial leads. The header assembly may be molded directly to the medical device or preformed and then attached to the device casing, either by mechanical fastener and/or chemical adhesive.

11 Claims, 13 Drawing Sheets

ONE PIECE HEADER ASSEMBLY FOR AN IMPLANTABLE MEDICAL DEVICE

CROSS REFERENCE TO RELATED APPLICATIONS

This application claims priority based on provisional applications Ser. Nos. 60/267,764, filed Feb. 8, 2001 and 60/309,411 filed Aug. 1, 2001.

BACKGROUND OF THE INVENTION

1. Field of the Invention

The invention relates to a one-piece header assembly for connecting implantable medical devices to a body organ intended to be assisted by the medical device. The header assembly includes terminal blocks which connect directly to feedthrough wires extending from inside the medical device to a conductor leading to the body organ or tissue being assisted.

2. Prior Art

Header assemblies for implantable medical devices generally comprise feedthrough conductors in the form of pins or wires connected to the internal components of the medical device. The feedthrough wires extend through a wall of the medical device housing, such as a lid, and are electrically insulated therefrom by a ceramic-to-metal seal, and the like. Electrical continuity is established by connecting intermediate conductor wires between the feedthrough wires and connector blocks in the header assembly. Examples of this type of header assembly are shown in U.S. Pat. No. 4,254,775 to Langer, U.S. Pat. No. 4,262,673 to Kinney et al., U.S. Pat. No. 4,764,132 to Stutz, Jr., U.S. Pat. No. 5,282,841 to Szyszkowski and U.S. Pat. No. 5,336,246 to Dantanarayana.

The intermediate conductor wires represent an electrical connection that could fail through improper connection, corrosion, breakage, and the like. The header assemblies of the present invention eliminate the intermediate conductors. Instead, the feedthrough wires from the medical device connect directly to terminal blocks in the header assembly. This is a more reliable construction than those of the conventional designs.

SUMMARY OF THE INVENTION

The present invention is, therefore, directed to a header assembly for a medical device. The header assembly serves as a structure supporting the electrical connection between feedthrough wires extending from inside the medical device to a conductor connected to the body organ or tissue being assisted. Several different embodiments of header assemblies are described including those which are molded directly onto the lid of the medical device and pre-molded ones which are later secure to the medical device. In either case, the present header assemblies include terminal blocks which connect directly to the feedthrough wires coming from the medical device. This eliminates the need for an intermediate conductor wire connecting between the feedthrough wires and the terminal blocks as in the prior art devices.

These features of the present invention will be apparent upon consideration of the following detailed description thereof presented in connection with the following drawings.

DETAILED DESCRIPTION OF THE PREFERRED EMBODIMENTS

Referring now to the drawings, FIGS. 1 to 7 illustrate a header assembly 10 according to the present invention comprising at least one pair of terminal blocks 12 and 14 partially surrounded by a molded polymeric header 16 connected to an implantable medical device 18. The terminal blocks 12, 14 provide for connecting a co-axial conductor 20 from the medical device to a body tissue. The implantable medical device 18 is exemplary of any one of a number of known assist devices such as cardiac defibrillators, cardiac pacemakers, drug pumps, neurostimulators, hearing assist devices, and the like.

Figure 3:
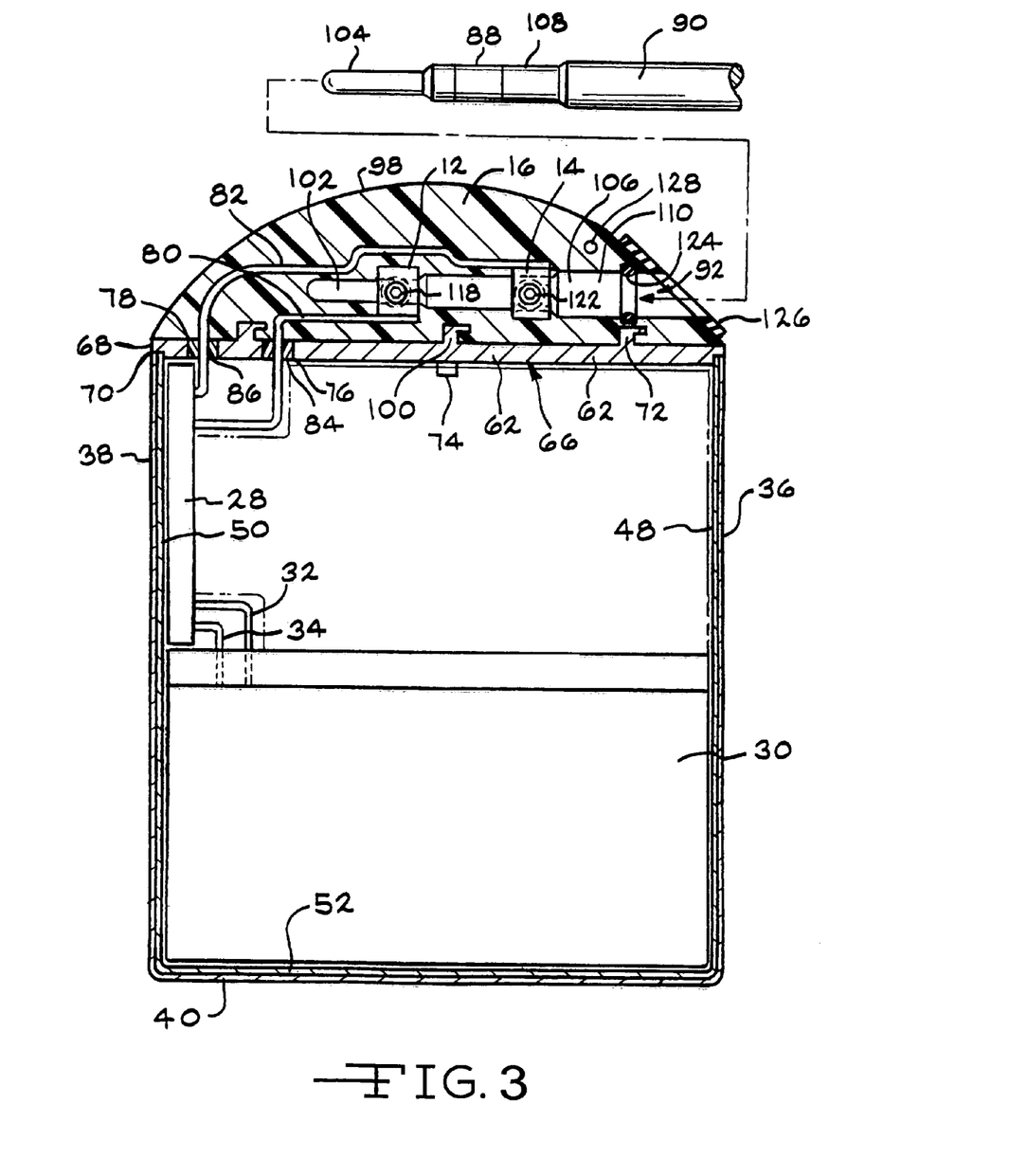
FIG. 3 is a sectional view taken along line 3—3 of FIG. 2.
Figure 4:
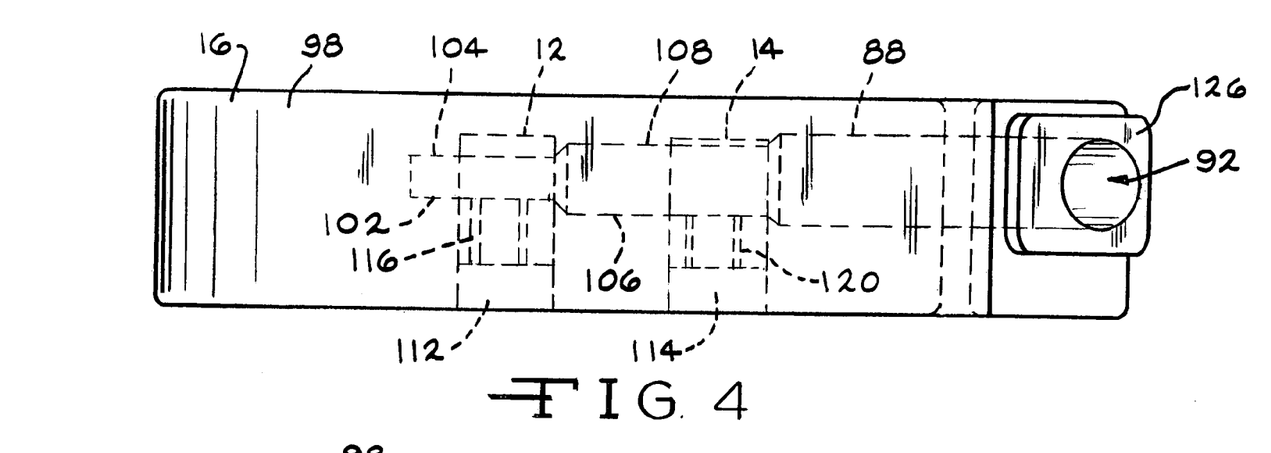
FIG. 4 is a plan view, partly in phantom, of the header assembly 10.
Figure 5:
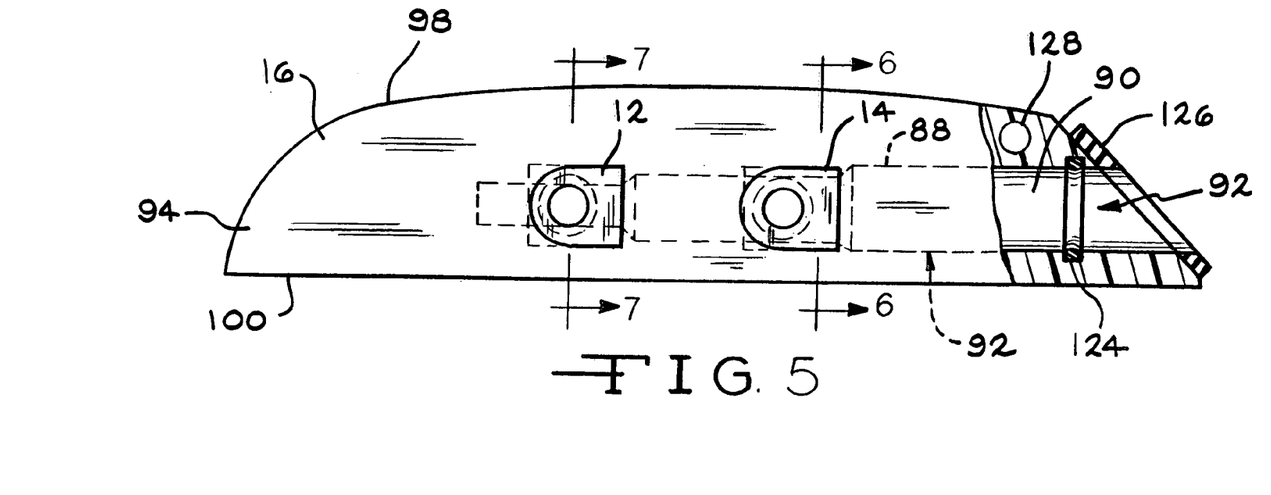
FIG. 5 is a side elevational view of the header assembly 10.
Figure 6:
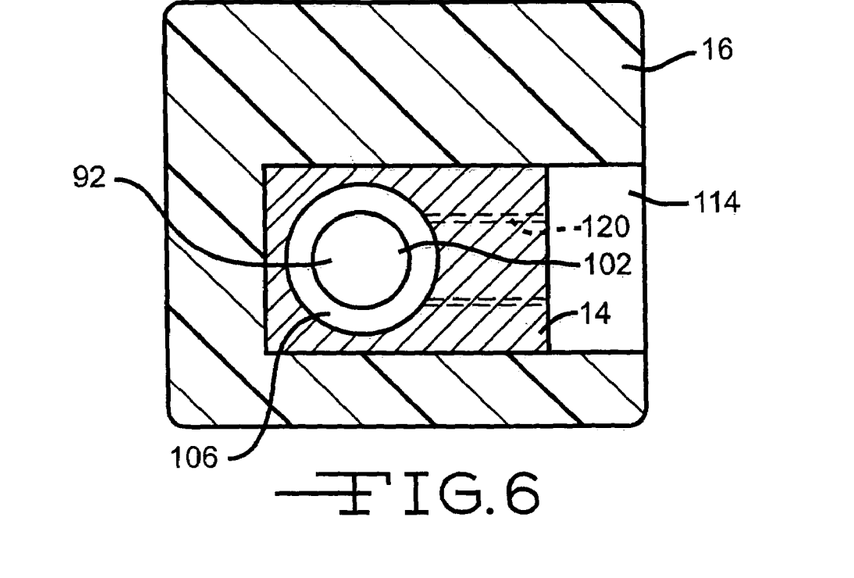
FIG. 6 is a sectional view taken along line 6—6 of FIG. 5.
Figure 7:
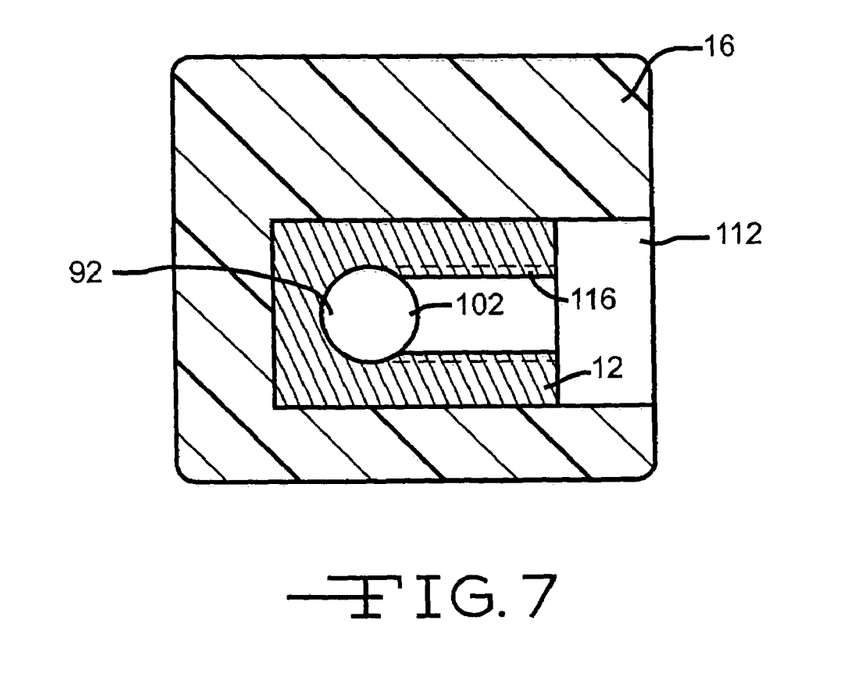
FIG. 7 is a sectional view taken along line 7—7 of FIG. 5.

The implantable medical device 18 is contained in a housing 22 of a material such as of stainless steel, and is shown in an exemplary form comprising first and second main clam shell portions 24 and 26. The clam shells 24 and 26 are mated together and hermetically sealed about their periphery to provide an enclosure for the medical device including its control circuitry 28 and a power supply 30 such as a battery (FIG. 3). The battery 30 is connected to the control circuitry 28 by electrical leads 32 and 34. There may also be a capacitor for a medical device such as a defibrillator.

In particular, the first clam shell 24 comprises spaced apart side walls 36 and 38 extending to and meeting with end wall 40. The side walls 36, 38 and the end wall 40 meet each other at rounded corners and extend to a front wall 42. Opposite the front wall 42 is a peripheral edge 44 of side walls 36, 38 and end wall 40 while opposite the end wall 40 is an opening 46.

The second clam shell 26 comprises spaced apart side walls 48 and 50 (FIG. 3) extending to and meeting with end wall 52. The side walls 48 and 50 and end wall 52 meet at rounded corners and extend to front wall 54. Opposite the front wall is a peripheral edge 56 of the side walls 48 and 50 and end wall 52 while opposite the end wall 52 is an opening 58. The first clam shell 24 is sized to fit inside the periphery of the second clam shell 26 in a closely spaced, lap joint relationship. This assembly forms a container having an opening 60 leading therein where the coinciding openings 46 and 58 of the respective clam shells 24 and 26 reside. The container opening 60 has a generally rectangular shape.

The benefit of having a lap joint construction for the mating clam shells 24 and 26 is that when they are hermetically sealed together, such as by laser welding, the laser beam is prevented from compromising the control circuitry 28 and power supply 30 of the medical device. With a coplanar or butted seam construction (not shown), it is possible for the laser beam to penetrate past the junction of the peripheral edges 44, 56 of the clam shells 24, 26 to compromise the internal device components or power supply housed therein. If a butt welded construction is used, a backing ring (not shown) is desired. An example of a backing ring for a butt weld construction is shown in FIG. 14 of U.S. Pat. No. 6,334,879 to Muffoletto et al., which is assigned to the assignee of the present invention and incorporated herein by reference.

A lid 62 is hermetically sealed to the opening 60 of the mated clam shells 24, 26. The lid 62 consists of spaced apart upper and lower surfaces 64 and 66 extending to and meeting with a surrounding edge 68 (FIG. 3). The surrounding edge 68 includes an inverted step or rim 70 to assist in the sealing connection between the lid 62 and the mated clam shells 24, 26. Preferably, the lid 62 is sealed in place, such as by laser welding (not shown), to create the hermetic housing 22 for the implantable medical device 18.

While the medical device is shown being contained inside a housing of mating clam shells 24, 26, the present invention is not intended to be so limited. Other types of housings such as prismatic, deep drawn, cylindrical are also contemplated.

Figure 1:
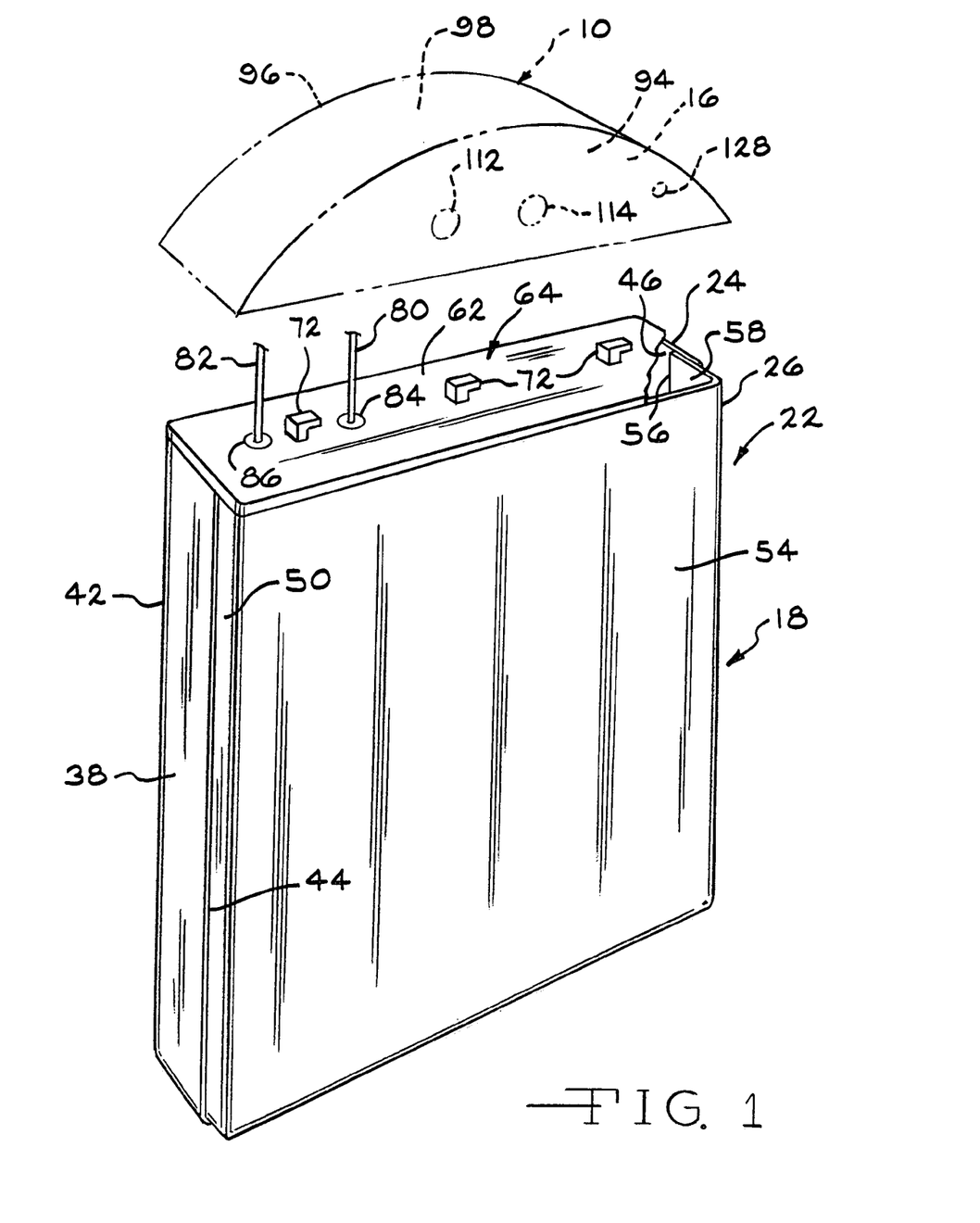
FIG. 1 is an exploded view of a header assembly 10 for an implantable medical device 18.
Figure 2:
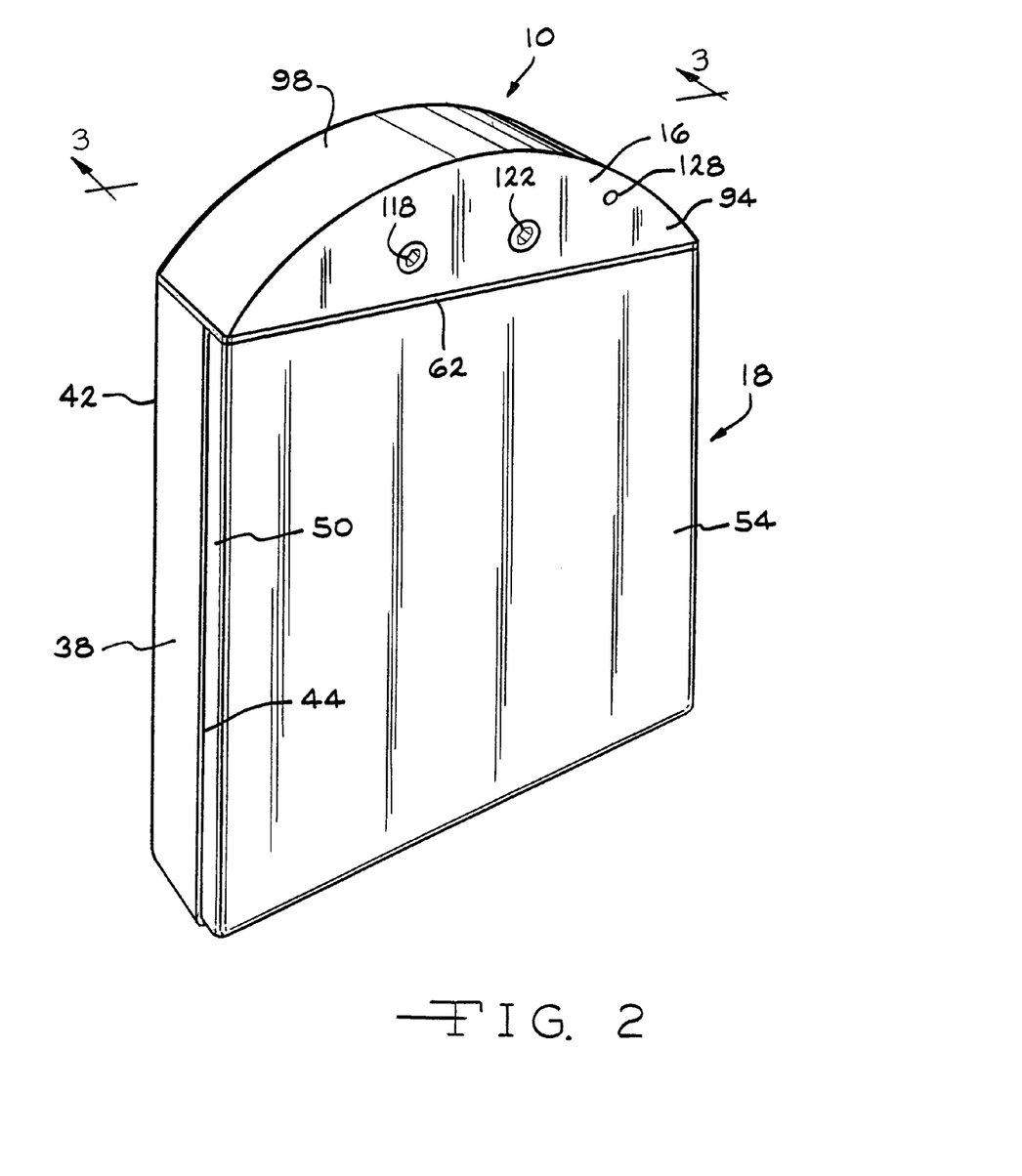
FIG. 2 is a perspective view of the header assembly 10 and medical device 18 shown in FIG. 1.

As shown in FIGS. 1 and 3, the upper surface 64 of the lid 62 includes a plurality of protruding anchors 72 which assist in joining the header 10 to the lid. Internal protrusions 74 depend from the lower lid surface 66 and assist in positioning the lid on the mated clam shells.

The lid 62 further comprises at least two openings 76 and 78 through which respective feedthrough wires 80 and 82 pass. The feedthrough wires extend from a distal end positioned inside the housing 22 connected to the control circuitry 28 for the medical device 18 to respective proximal ends disposed generally parallel to and spaced above the upper surface 64 of the lid 62. The feedthrough wires 80, 82 are electrically insulated from the lid 62 by respective ceramic-to-metal seals or glass-to-metal seals 84 and 86.

The proximal end of feedthrough wire 80 is connected to the first terminal block 12 supported thereon while the other feedthrough wire 82 is connected to a second terminal block 14 depending therefore. The terminal blocks 12, 14 are ring-shaped members of different diameters, sized to be in electrical contact with matching portions of the lead 88 for a co-axial conductor 90, as will be described in detail hereinafter.

As shown in FIG. 3, the terminal blocks 12 and 14 are aligned in a co-axial relationship and encased in the molded header 16 having a bore 92 providing communication to both of them. The molded header 16 comprises spaced apart front and back walls 94 and 96 extending to a curved upper wall 98 and a generally planar bottom wall 100. The bottom wall 100 is supported on the upper lid surface 64 and retained in place by encasing the lid anchors 72. The bore 92 is sized to receive the co-axial conductor lead 88. Those skilled in the art will readily understand that the exact shape of the molded header is exemplary. In fact, the molded header can have a myriad of different shapes only limited by the design specifications of the associated medical device and its intended use.

In that respect, the header assembly bore 92 has a first portion 102 of a first diameter sized to receive a distal portion 104 of the conductor lead 88, a second, intermediate portion 106 of a second, greater diameter sized to receive a proximal portion 108 of the lead 88 and a third portion 110 of a still greater diameter than the intermediate portion. The terminal blocks 12, 14 have lead openings of diameters somewhat larger than the first and second bore portions 102, 106 so that the conductor lead 88 is received therein in a tight fitting, electrically stable connection.

The front wall 94 of the molded header 16 is provided with a pair of passageways 112 and 114 aligned perpendicularly with the longitudinal axis of the bore 92. Passageway 112 extends to a threaded aperture 116 in the side wall of terminal block 12 to provide for communication with the first bore portion 102. The passageway and aperture threadingly receive a set screw 118 that contacts the distal portion 104 of the conductor lead 88 to prevent loss of electrical contact between the lead and the terminal block 12. Similarly, passageway 114 extends to a threaded aperture 120 in the side wall of terminal block 14 to provide for communication with the second bore portion 106. A set screw 122 is received therein to contact the proximal portion 108 of the conductor lead 88, thereby maintaining electrical continuity between the lead and the terminal block 14.

An annular channel surrounds the third bore portion 110 for capturing an O-ring 124 therein. This helps to prevent body fluids and the like from contacting the conductor portions 104 and 108 received in the respective terminal blocks 12 and 14. A raised seal 126 further helps prevent body fluids from contacting the co-axial conductor lead 88. Finally, the header assembly 10 is provided with a suture bore 128 adjacent to the conductor lead bore 92. The suture bore 128 aids a physician in securing the medical device inside a body.

As known in the art, the end (not shown) of the co-axial conductor 90 opposite that of the lead 88 is positioned in a body tissue, such as a heart muscle, for transmitting physiological information to the medical device and for administering a medical theory as needed. An example of this is in a cardiac defibrillator where the medical device may monitor the heart rate for extended periods of time. Then, when a potentially fatal irregular, rapid heartbeat known as tachyarrhythmia is detected, the defibrillator delivers an electrical shock to the heart through the lead 88 and conductor 90.

Figure 8:
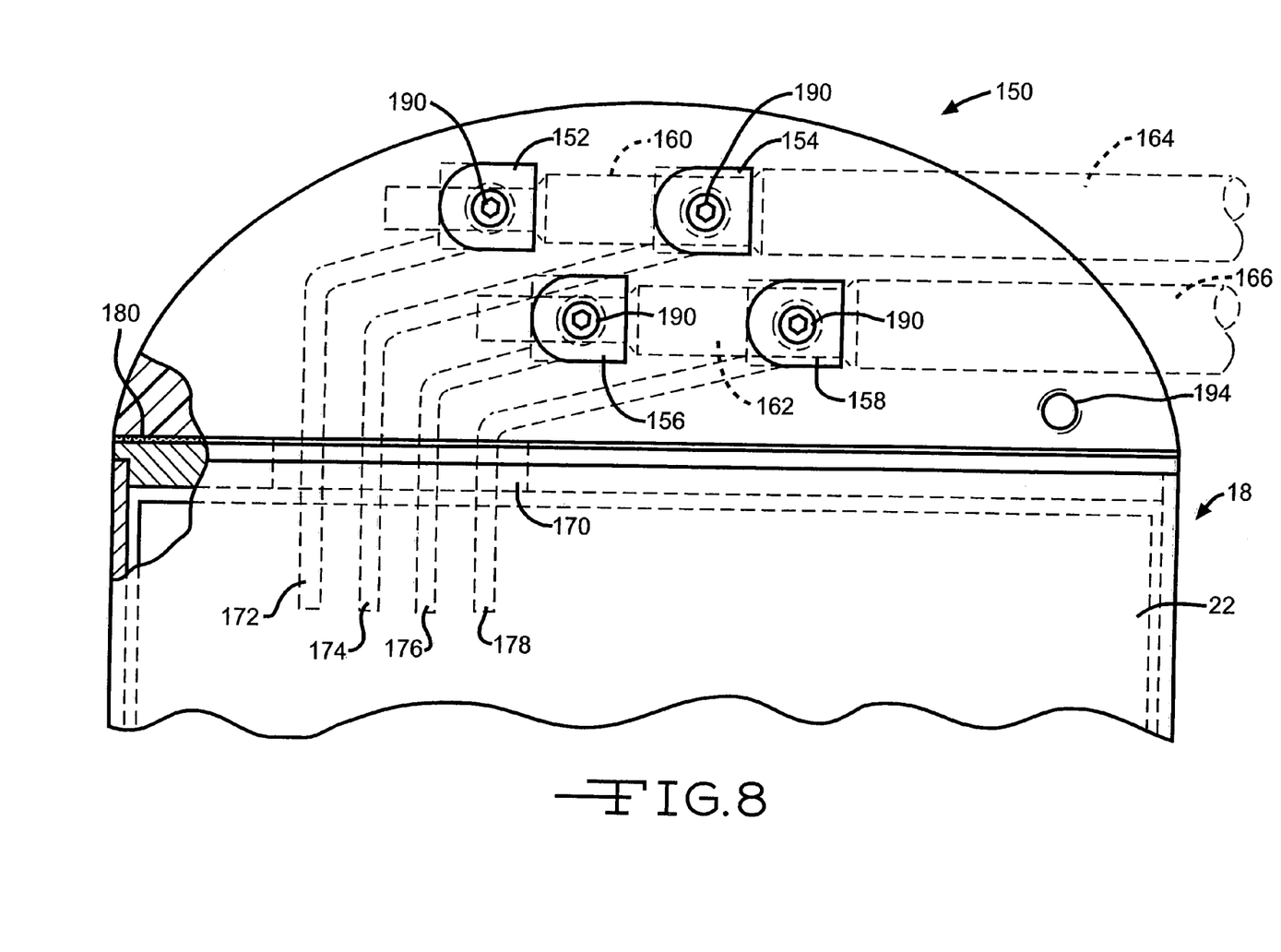
FIG. 8 is an elevational view, partly in section and partly in phantom, of a header assembly 150 according to the present invention for the medical device 18.
Figure 9:
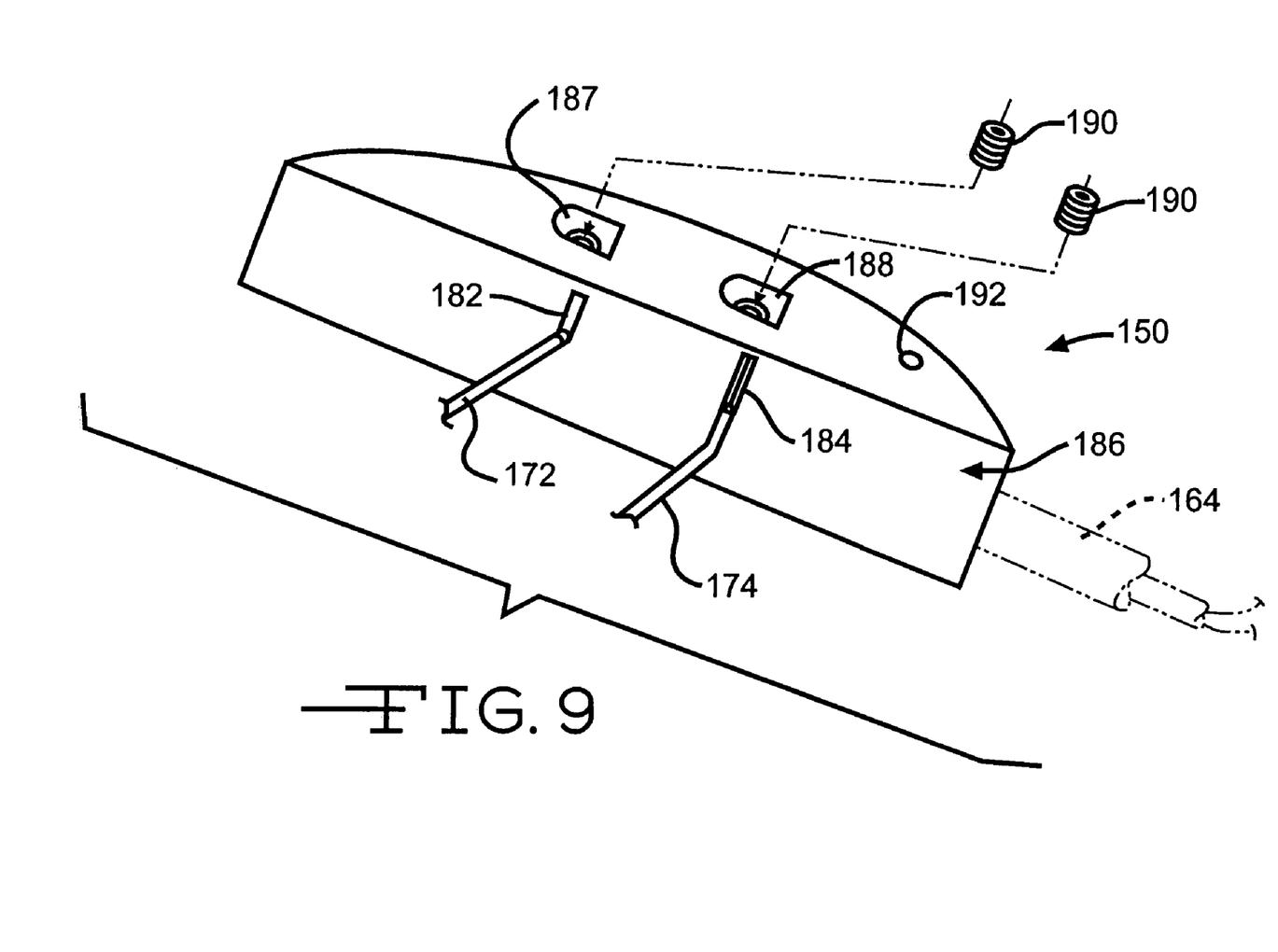
FIG. 9 is a perspective view of the header assembly 150 connected to feedthrough wires 172, 174 from the medical device.

FIGS. 8 and 9 show a further embodiment of a header assembly 150 according to the present invention. The header assembly 150 comprises a polymeric material supporting a first pair of terminal blocks 152 and 154 and a second pair of terminal blocks 156 and 158. The terminal block pairs have lead openings aligned co-axially along respective conductor bores sized to receive the conductor leads 160 and 162 of co-axial conductors 164 and 166. The lid 168 is provided with a ceramic-to-metal seal 170 that electrically insulates feedthrough wires 172, 174, 176 and 178 from the lid 168. The feedthrough wires are in electrical contact with respective terminal blocks 152, 154 156 and 158.

In this respect, the header assembly 150 is similar to the header assembly 10 of FIGS. 1 to 8 except there are two pairs of terminal blocks instead of one. Those skilled in the art will understand that a header assembly according to the present invention can have terminal blocks in addition to the one or two pairs shown. There can be three, four or more pairs. Additionally, it may be desired to have a header assembly where a bore only communicates with one terminal block which is not in a co-axial relationship with a second terminal block.

However, the header assembly 150 differs from the header assembly 10 in that it is not secured to the housing lid 168 by anchors. Instead, header assembly 150 is mounted to the lid 168 by an adhesive material 180, and the like. As shown in FIG. 9, this necessitates that the header assembly 150 include passageways 182 and 184 extending from the lower surface 186 thereof to communicate with the terminal blocks. For the sake of clarity, this drawing only shows one set of passageways for one of the feedthrough wire pairs 172, 174. However, those skilled in the art will understand that there are as many passageways as there are terminal blocks and associated feedthrough wires.

In that respect the feedthrough wires 172, 174 are received in the passageways 182, 184 to contact respective terminal blocks, 152, 154 when the header assembly 150 is supported on the lid 168. A laser beam as a joining device is then directed through the side passageways 187, 188 to weld the feedthrough wires in place, electrically contacted to the terminal blocks. Other joining means are contemplated such as soldering, brazing, epoxy, and the like.

A co-axial conductor 164 is then inserted into the header assembly 150 in electrical contact with the terminal blocks, as previously discussed with respect to header assembly 10 shown in FIGS. 1 to 7. The lead of the co-axial conductor 164 is retained in place in the terminal blocks by respective set screws 190 extending through passageways 186, 188 and apertures in the side walls of the terminal blocks to contact the conduction leads.

Another distinction between the header assemblies 10 and 150 is the method of closing the housing for the medical device in the latter embodiment. In the case of header assembly 150, the feedthrough wires are connected to the terminal blocks before being connected to the medical device circuitry. This necessitates that the hermetic housing be constructed by first mounting the lid 168 on one of the clam shells 24, 26. The header assembly 150 is then secured to the lid 168 such as by adhesive, and the like. Next, the feedthrough wires are connected to the internal components of the medical device. Finally, the other clam shell is mated to the first clam shell and sealed thereto to complete the hermetic housing. A suture bore 192 is also provided.

Figure 10:
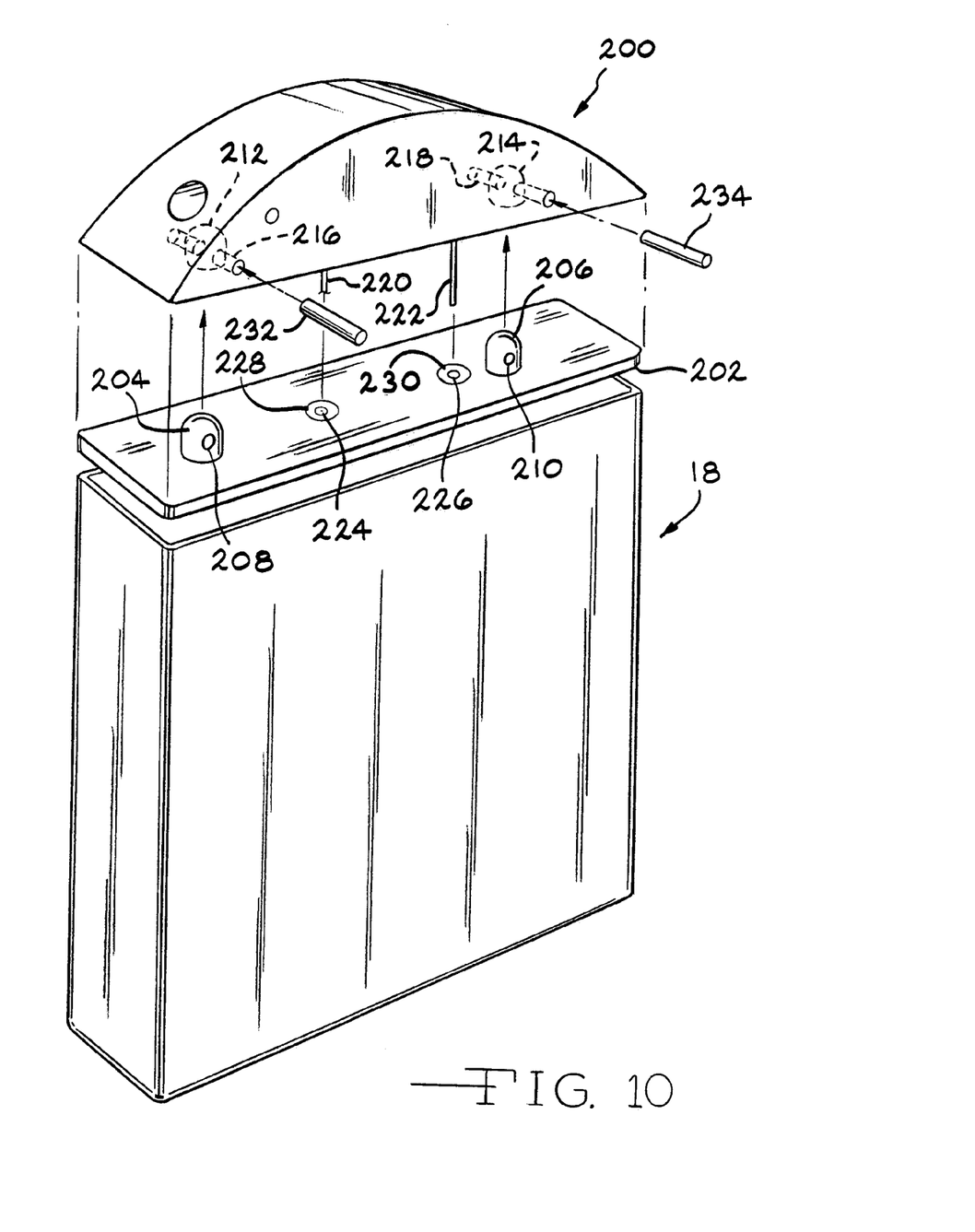
FIG. 10 shows the header assembly being secured to the casing by a mechanical fasteners.

FIG. 10 shows another embodiment of a header assembly 200 according to the present invention. This header assembly is similar to the header assembly 150 of FIGS. 8 and 9 in that it is not molded to anchors provided on the lid. Rather, header assembly 200 is molded as a separate piece and later connected to a lid 202 having first and second upstanding lugs 204 and 206. The lugs 204, 206 are provided with through apertures 208 and 210 generally aligned parallel to the upper surface of the lid 202.

The header is provided with a pair of spaced apart inlets 212 and 214 sized and positioned to receive the lugs 204, 206. The header assembly 200 is further provided with through bores 216 and 218, which align with the apertures 208, 210 when the header assembly is positioned on the lid 202. As the header assembly 200 is positioned on the lid 202, feedthrough wires 220 and 222 previously connected to the terminal blocks (not shown) by welding through setscrew passageways (not shown) are received in respective openings 224, 226 in the lid. As in the other header assembly embodiments, the wires 220, 222 are insulated from the lid by ceramic-to-metal seals 228, 230, and the like. Pins 232 and 234 are then inserted into the respective through bores 216, 218 and apertures 208, 210 to complete the connection. Preferably, the exposed ends of the pins are sealed by a polymeric plug, such as a silicon septum plug, and the like, to prevent them from working loose and to provide a smooth outer surface for the header assembly.

Figure 11:
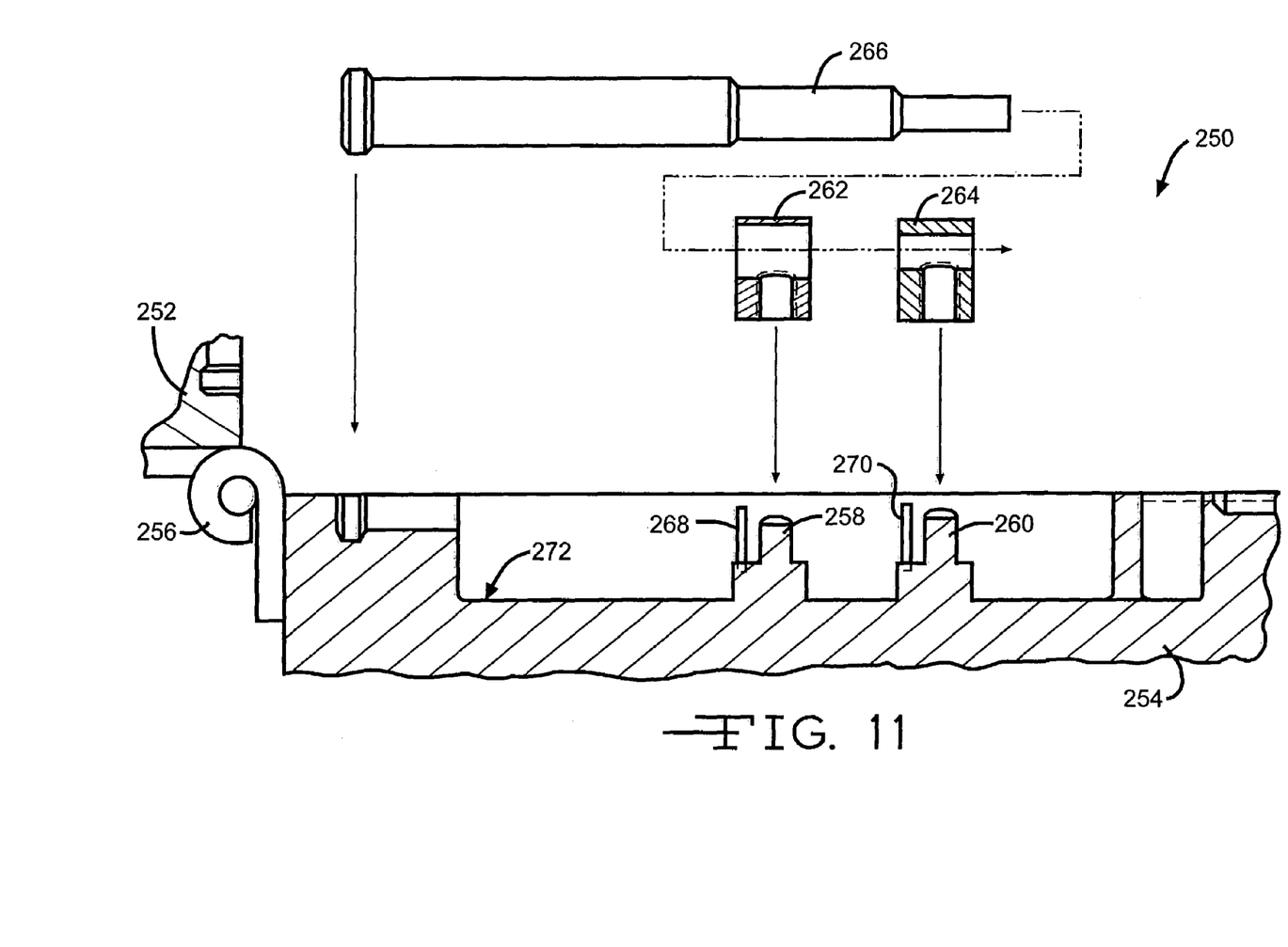
FIG. 11 is a cross-sectional view of a book mold 250 in an opened position for manufacturing a header assembly according to the present invention.
Figure 12:
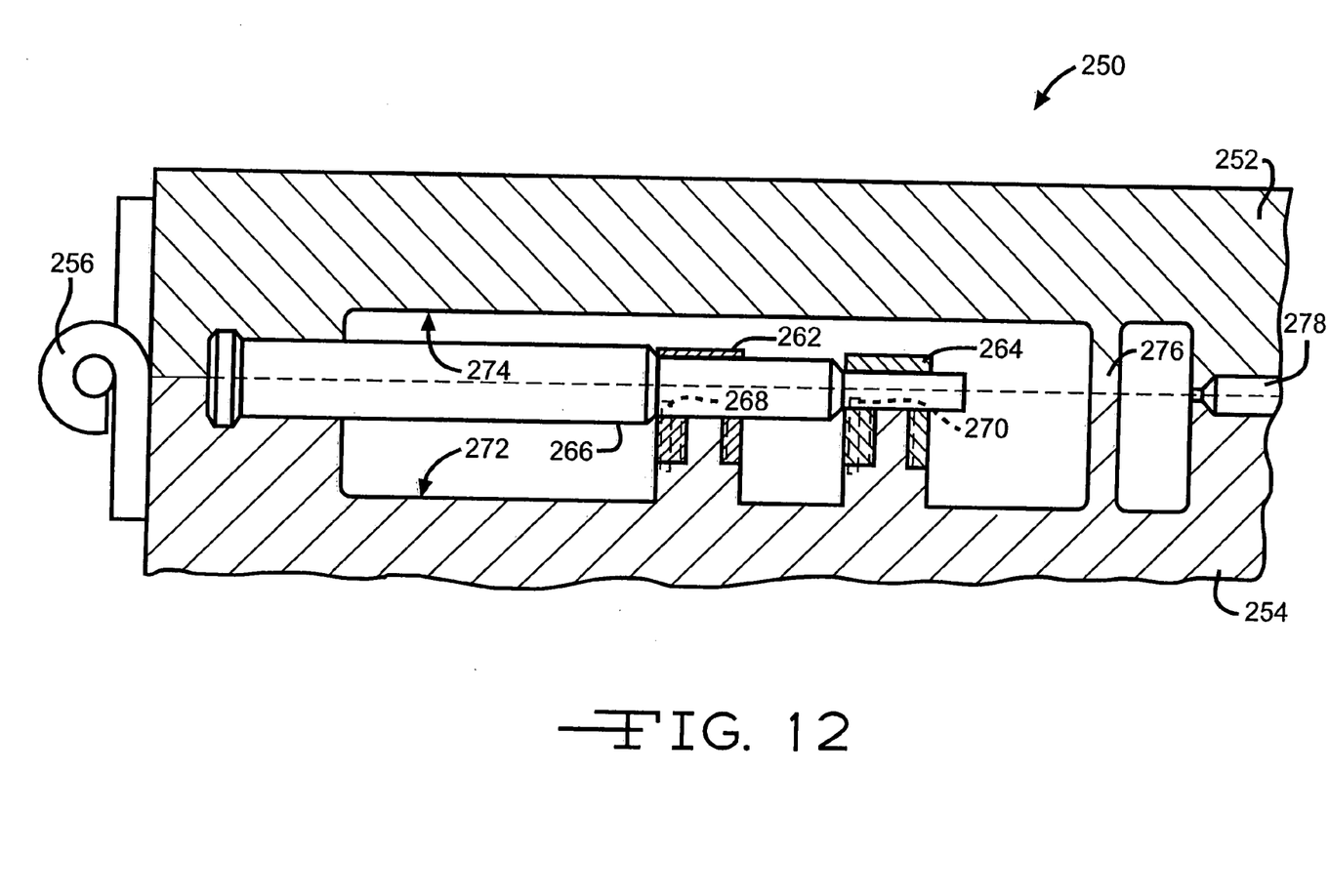
FIG. 12 is a cross-sectional view of the book mold 250 of FIG. 11 in a closed position.

FIGS. 11 and 12 show a book mold 250 for molding any one of the header assemblies 10, 150 and 200 according to the present invention. The book mold 250 comprises first and second mold portions 252 and 254 connected together by a hinge 256. The benefit of a book mold is that either or both of the first and second mold portions 252, 254 can be changed to provide a header assembly having a desired shape without necessarily having to change the entire mold.

The second mold portion 254 includes posts 258 and 260 on which respective terminal blocks 262 and 264 are supported. When the molding process is complete, the posts 258 and 260 coincide with the passageways through which the welds between the feedthrough wires and the terminal blocks are made for header assemblies 150 and 200, and the apertures which receive set screws for securing the electrical connection between the lead of a co-axial conductor and the terminal blocks for all of the present invention header assemblies.

A pin 266 having the shape of the lead of a co-axial conductor is positioned in the second mold portion 254 received in the respective terminal blocks 262 and 264. Inserts 268 and 270 are supported on the second mold portion 254 abutting the shaped pin 266 from the back of the mold portion, i.e., that portion of the mold lying in the plane of the paper for FIG. 11 and extending toward the reader. These inserts 268, 270 coincide with passageways 182, 184 for the header assembly 150. The second mold portion 254 is then secured to the first mold portion 252 to provide a cavity having the shape of the to be manufactured header assembly. In that respect, the header assembly is formed laying on its side such that surface 272 of the second mold portion 254 forms the front wall 94 of header assembly 10 while surface 274 of the first mold portion 252 forms the back wall 96 thereof. Mold structure 276 forms the suture openings of the various header assemblies.

The closed book mold 250 is provided with a channel 278 which mates with the barrel of a molding machine (not shown) to inject a charge of polymeric material therein to form the header assembly. Various polymeric materials are contemplated by the scope of the present invention including high durometer polyurethane or polysulfane resins.

Figure 13:
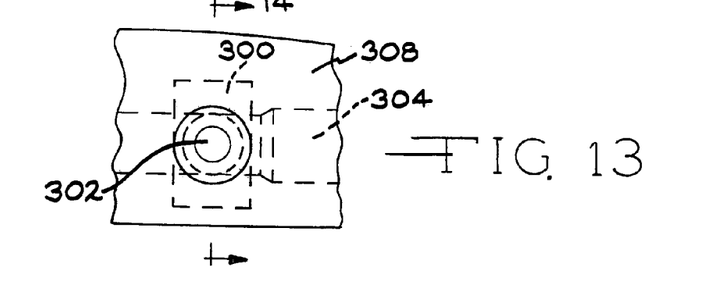
FIG. 13 is a broken away view, partly in phantom, of another embodiment of a terminal 300 according to the present invention.
Figure 14:
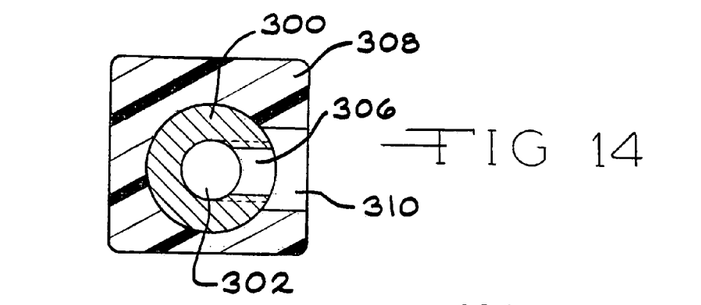
FIG. 14 is a cross-sectional view along line 14—14 of FIG. 13.

FIGS. 13 and 14 show another embodiment of a terminal sleeve 300 for connecting a feedthrough wire to the lead of a conductor according to the present invention. Terminal sleeve 300 is a generally cylindrical member having a lead opening 302 disposed along its longitudinal axis and aligned along a bore 304 for the lead. A threaded aperture 306 receives a set screw (not shown) and the like, for securing the lead inside sleeve 300. The sleeve is supported in a body 308 of polymeric material having a passageway 310 aligned with the aperture 306. The passageway 310 serves to admit a joining device, such as a laser, for welding the feedthrough wire to the sleeve 300 and for positioning the set screw in the threaded aperture 306.

Figure 15:
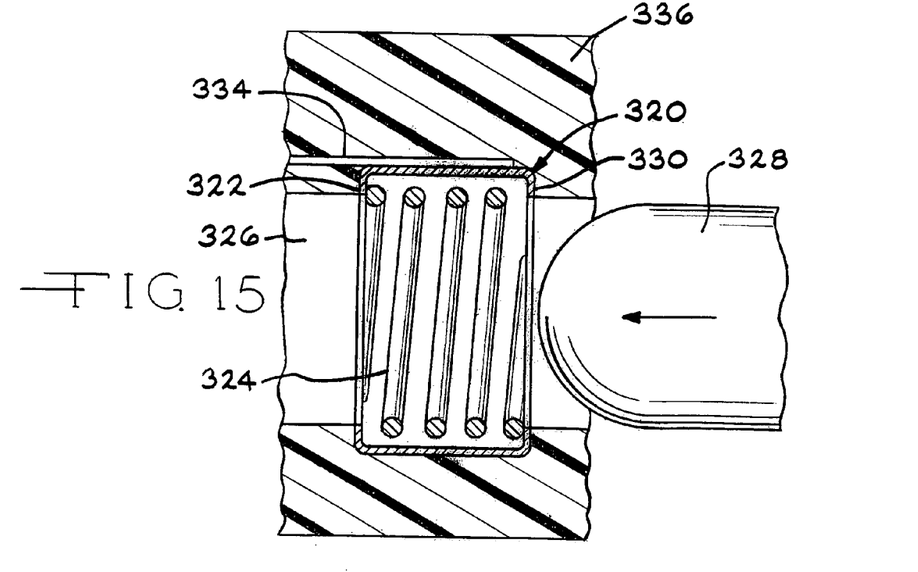
FIG. 15 is sectional view of another embodiment of a terminal 320 prior to a lead 328 being inserted therein.
Figure 16:
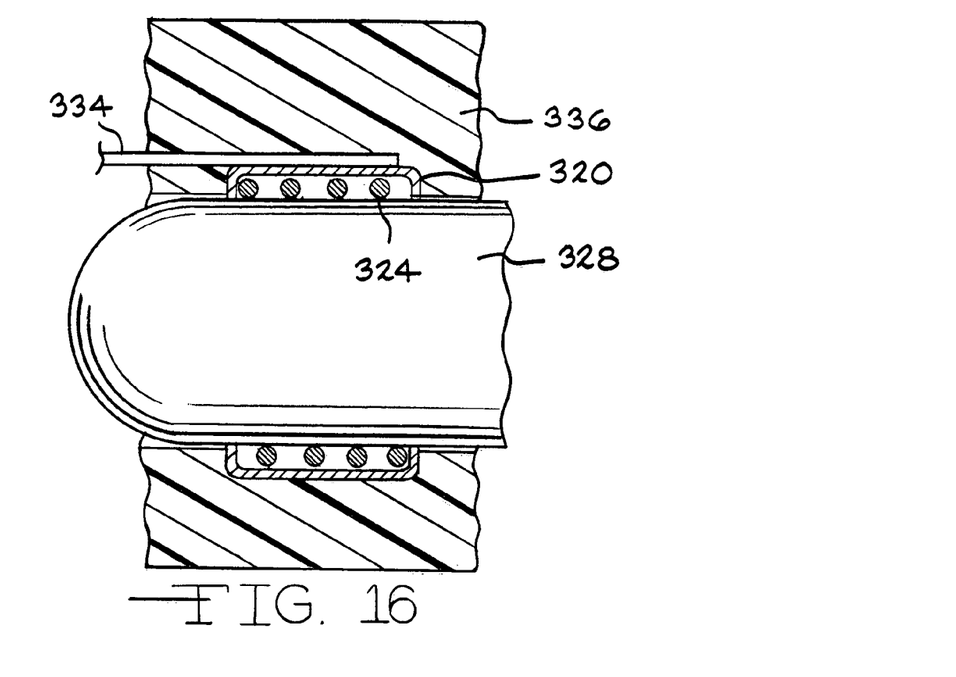
FIG. 16 is a sectional view of the terminal of FIG. 15 with the lead 328 received therein.

FIGS. 15 and 16 show another embodiment of a terminal 320 comprising a cylinder 322 supporting an internal coil spring 324. The cylinder 322 and spring 324 have coincident openings aligned along a bore 326 for receiving the lead 328 of a conductor. The opposed ends 330 and 332 of the cylinder are curled inwardly to retain the coil spring in place. When the lead 328 is moved along the bore 326 and into the terminal 320, the spring expands in a radial manner to capture the lead therein in a tight-fitting relationship. This terminal eliminates the need for a set screw, and the like, although one can be used if desired. A feedthrough wire 334 is connected to the terminal supported in a body of polymeric material 336.

Figure 17:
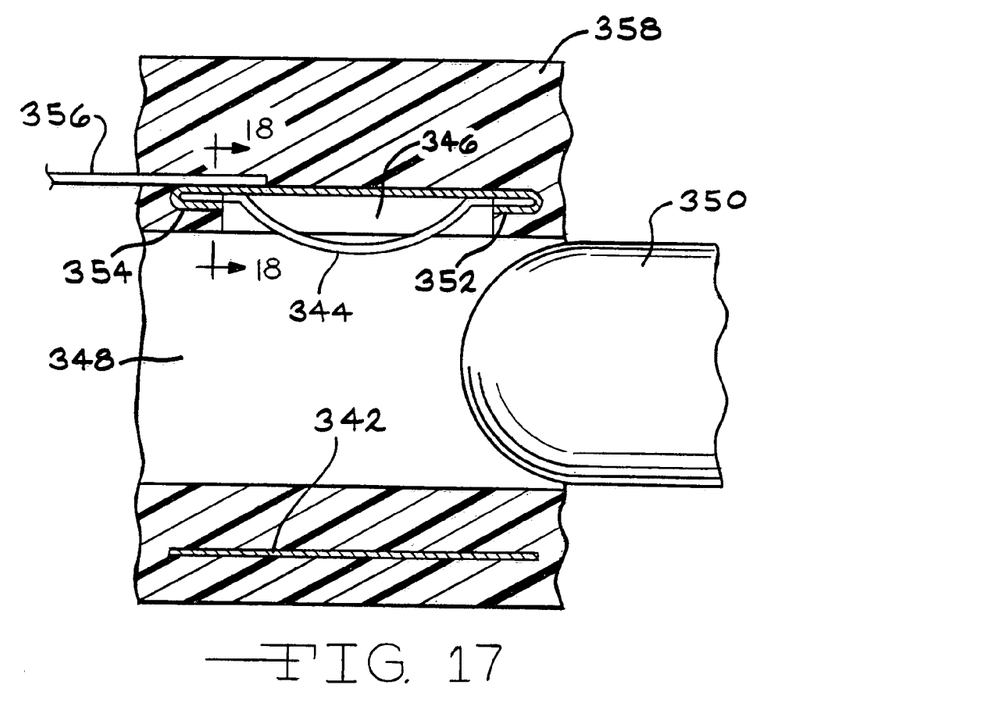
FIG. 17 is a sectional view of another embodiment of a terminal 340 prior to a lead 350 being inserted therein.
Figure 18:
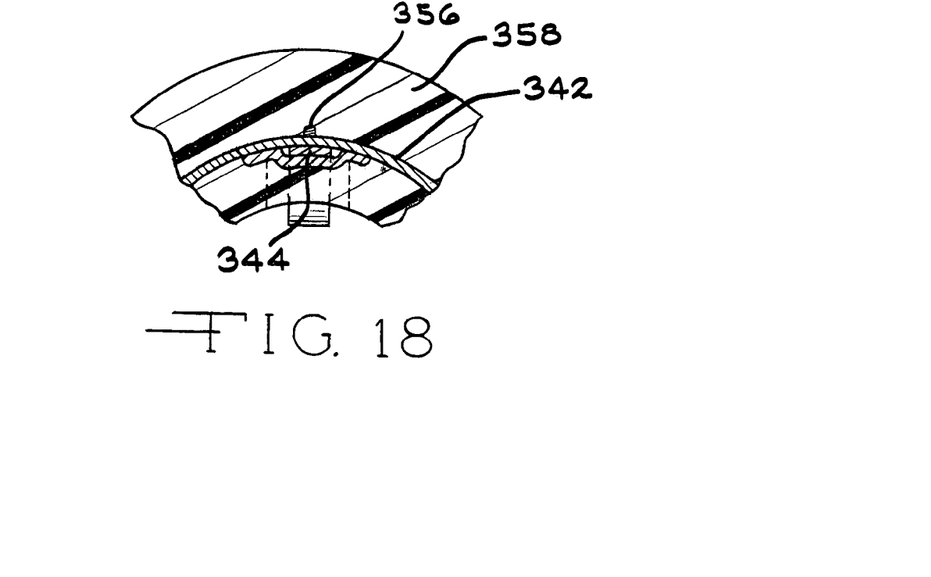
FIG. 18 is a cross-sectional view along line 18—18 of FIG. 17.
Figure 19:
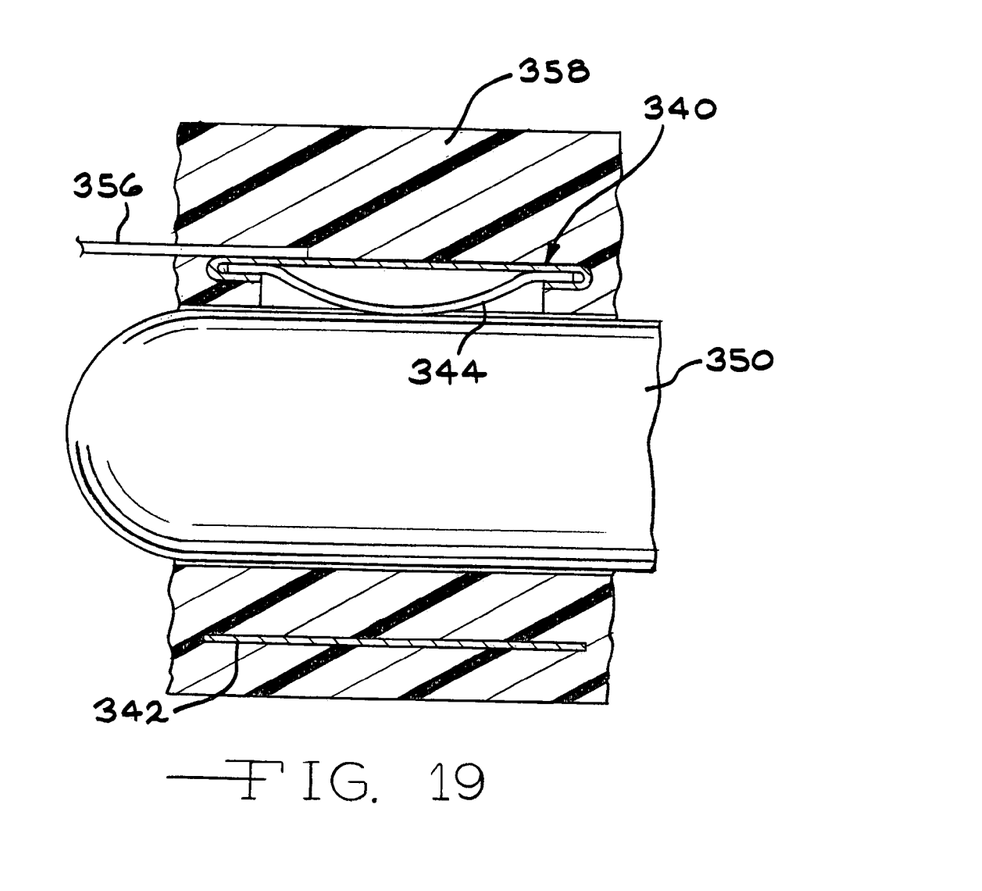
FIG. 19 is a sectional view of the terminal of FIGS. 17 and 18 with the lead 350 received therein.

FIGS. 17 to 19 illustrate another embodiment of a terminal 340 comprising a cylinder 342 supporting at least one leaf spring 344. The cylinder 342 has an opening 346 aligned along a bore 348 for receiving the lead 350 of a conductor. The opposed ends 352 and 354 of the cylinder are crimped to retain the leaf spring in place, disposed parallel to the longitudinal axis of the bore 348. When the lead is moved along the bore 348 and into the terminal 340, the leaf spring 344 deflects to exert a biasing force on the lead captured therein. The ends of the leaf spring are captured in the cylinder such that the spring does not misalign as the lead moves into and out of the cylinder 342 and bore 348. This terminal eliminates the need for a set screw, although one can be used if desired. A feedthrough wire 356 is connected to the terminal supported in a body of polymeric material 358.

Now, it is therefore apparent that the present invention accomplishes its intended objects. While embodiments of the present invention have been described in detail, that is for the purpose of illustration, not limitation.

What is claimed is:

1. A header assembly for connecting a conductor terminating at a body organ with control circuitry and at least one electrical energy storage device of an implantable medical device, the header assembly comprising:
   (a) a first electrically conductive terminal having a first lead opening sized to receive a first portion of a lead for the conductor;
   (b) a second electrically conductive terminal having a second lead opening sized to receive a second portion of the lead for the conductor;
   (c) a body of polymeric material molded as a single piece to support the first and second terminals in a partially encased relationship so that the first and second terminals are prevented from moving by the polymeric material;
   (d) a first bore communicating from outside the polymeric body to the first and second lead openings aligned in a first co-axial relationship;
   (e) a first passageway extending into the body leading to the first terminal, and wherein a second passageway extends into the body in communication with the first terminal and the first passageway;
   (f) a third passageway extending into the body leading to the second terminal, and wherein a fourth passageway extends into the body in communication with the second terminal and the third passageway; and
   (g) wherein the first and third passageways are in communication with the second and fourth passageways and provide for receiving a feedthrough wire that is directly contactable to the respective first and second terminals.

2. The header assembly of claim 1 wherein the body further supports third and fourth terminals having third and fourth lead openings aligned in a second co-axial relationship along a second bore communicating from outside the body to the third and fourth terminals.

3. The header assembly of claim 2 wherein the first co-axial relationship of the first and second lead openings along the first bore is offset with respect to the second co-axial relationship of the third and fourth lead openings aligned along the second bore.

4. The header assembly of claim 1 wherein the first bore is sized to receive the lead of the conductor in the first and second lead openings of the first and second terminals.

5. The header assembly of claim 1 wherein the first bore includes an annular channel supporting an O-ring for sealing about the lead of the conductor received in the first and second lead openings.

6. The header assembly of claim 1 wherein the electrical energy storage device is selected from a battery and a capacitor.

7. The header assembly of claim 1 wherein the medical device is selected from the group consisting of a hearing assist device, neurostimulator, cardiac pacemaker, drug pump, and cardiac defibrillator.

8. The header assembly of claim 1 wherein the first and second terminals are selected from the group consisting of a terminal block, a sleeve, a ring-shaped member supporting a coil spring and a ring shaped member supporting at least one leaf spring.

9. The header assembly of claim 1 wherein first and second feedthrough wires extending from the medical device are connectable to the first and second terminals through the respective first and third passageways.

10. The header assembly of claim 1 wherein the polymeric material is selected front the group consisting of high durometer polyurethane and polysulfane resins.

11. The header assembly of claim 1 wherein a first threaded aperture and a second threaded aperture are provided in the respective first and second terminals in communication with the respective second and fourth passageways.

* * * * *